United States Patent [19]

Macho et al.

[11] 4,103,041
[45] Jul. 25, 1978

[54] PROCESS FOR COATING SLIDES

[75] Inventors: Heinz Macho, Mannheim-Neuostheim; Hans Lange, Lampertheim; Dieter Berger, Viernheim; Wolfgang Werner, Mannheim-Vogelstang, all of Germany

[73] Assignee: Boehringer Mannheim GmbH, Mannheim, Germany

[21] Appl. No.: 672,574

[22] Filed: Mar. 31, 1976

[30] Foreign Application Priority Data

Apr. 11, 1975 [DE] Fed. Rep. of Germany ....... 2515869

[51] Int. Cl.² .............................................. A01N 1/02
[52] U.S. Cl. ................................................ 427/2; 8/3;
350/92; 427/4; 427/282; 427/287; 427/424
[58] Field of Search ............... 427/282, 287, 2, 4, 427/424; 350/92; 8/3

[56] References Cited

U.S. PATENT DOCUMENTS

| | | | |
|---|---|---|---|
| 3,004,875 | 10/1961 | Lytle | 427/110 |
| 3,056,696 | 10/1962 | Browne | 427/287 |
| 3,495,926 | 2/1970 | Naz | 8/3 |
| 3,667,896 | 6/1972 | McCormick et al. | 350/92 |
| 3,796,594 | 3/1974 | Thomae et al. | 350/92 |
| 3,837,795 | 9/1974 | Becker et al. | 8/3 |
| 3,900,641 | 8/1975 | Woodman et al. | 427/282 |
| 3,906,120 | 9/1975 | Geating | 427/4 |
| 3,932,681 | 1/1976 | Forker et al. | 427/287 |

*Primary Examiner*—Ronald H. Smith
*Assistant Examiner*—Sadie L. Childs
*Attorney, Agent, or Firm*—Burgess, Dinklage & Sprung

[57] ABSTRACT

Pre-coated microscope slides are produced on a large scale by spraying a dyestuff solution on to microscope slides which are passed at a constant speed under a spray nozzle, the pattern of which is kept rectangular by means of a mask.

6 Claims, 3 Drawing Figures

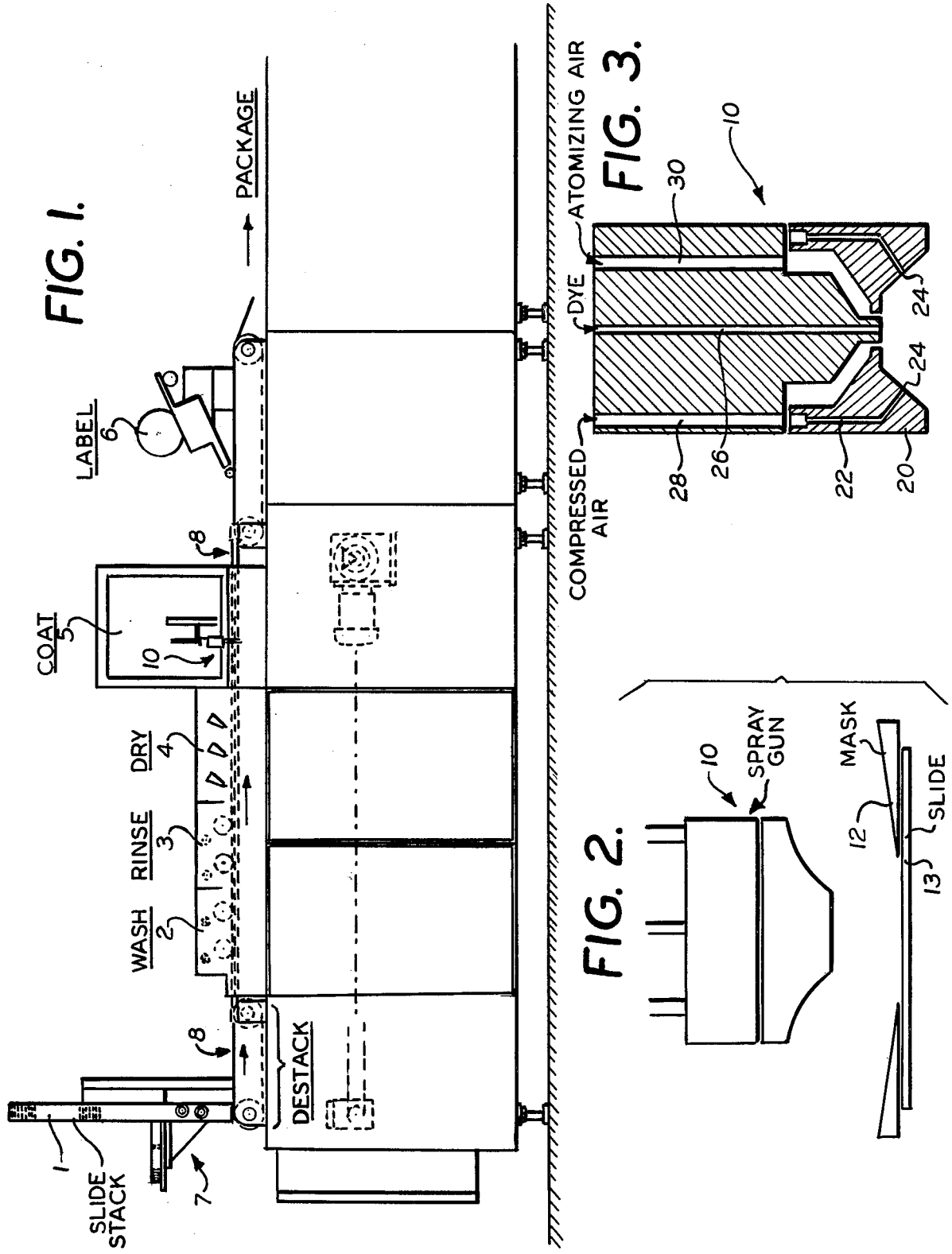

PROCESS FOR COATING SLIDES

BACKGROUND

This invention relates to a process and apparatus for the large-scale production of pre-coated microscope slides.

Pre-coated microscope slides have, in principle, been known for a long time. They are microscope slides coated with a layer of a dyestuff suitable for the purposes of microscopy. When a drop of liquid material to be stained is applied to such a microscope slide, then, after a certain period of time, the staining process commences.

The oldest examples of pre-colored microscope slides are those coated with brilliant cresyl blue for the so-called supravital staining of reticulocytes. They are prepared by manually coating microscope slides with a 1% alcoholic solution of brilliant cresyl blue, followed by drying. A drop of blood is smeared on to a so-treated microscope slide, which, after keeping for about 10 minutes in a moist chamber, is covered with a cover slip and then examined microscopically (cf, Pschyrembel, Klinisches Worterbuch, Berlin, 1969, p. 1287).

Pre-colored microscope slides have recently been described in U.S. Pat. No. 3,906,120 which are coated with new methylene blue (methylene blue N) and cresyl violet acetate. They are used for staining erythrocytes and leukocytes and give a differential blood count. This patent also describes, for the same purpose, microscope slides pre-coated with the dyestuffs methylene azure blue, methylene blue NN, cresyl violet acetate and toluidine blue O.

In all these cases, the dyestuffs are applied from an organic or aqueous solution in a thin film to the microscope slides and then dried. However, because of the inadequate wetting which sometimes occurs, this process gives rise to difficulties. Therefore, U.S. Pat. No. 3,906,120 requires the additional use of surface-active agents in order to avoid such wetting difficulties. The use of surface-active agents is admittedly possible in the case therein described but, in other cases, these agents could have a disturbing effect on the sensitive staining processes. A further disadvantage of all previously known pre-coated microscope slides is that hitherto they could only be produced manually in small numbers and, of course, considerable variations in quality had to be taken into account.

SUMMARY

It has now been found that pre-coated microscope slides of constant quality can be simply produced on a large scale, without having to take account of wetting difficulties, by spraying the dyestuff solutions on to microscope slides and drying immediately.

DESCRIPTION OF THE DRAWING

The present invention will be more fully understood from the following description taken in conjunction with the accompanying drawing wherein:

FIG. 1 is a side view and elevation of apparatus for producing pre-coated microscope slides according to the invention;

FIG. 2 is a partial front view of a portion of the apparatus shown in FIG. 1 showing the spray gun positioned over the mask and slide to be coated; and, FIG. 3 is a cross-sectional view of the spraying device used in the apparatus of the invention.

DESCRIPTION

According to the invention, an unbroken film is not formed but rather a very large number of microfine dyestuff droplets. These microfine dyestuff droplets can, depending upon the strength of the spraying, remain isolated from one another on the microscope slide or can also overlap one another. It is surprising that, even in the case of comparatively strong spraying, these droplets do not flow together and form an unbroken film so that all difficulties are thereby overcome which normally occur in the application of a liquid film due to insufficient wetting. Furthermore, it was not to have been foreseen that, with relatively simple means, it is possible to keep the amount sprayed on per unit surface area constant and homogeneous so that satisfactorily reproducible stainings are obtained with microscope slides precoated in this manner.

Thus, according to the present invention, there is provided a process for the large-scale production of precoated microscope slides, wherein a dyestuff solution is sprayed on to microscope slides.

In principle, spraying on can be carried out by all processes known for the homogeneous spraying of surfaces. In the case of the so-called one-component process, a solution is sprayed from a nozzle under high pressure. In the case of the two-component process, a solution emerges from a nozzle and is there atomized with the help of a compressed gas. The emergence of the liquid is hereby brought about either passively by the suction produced by the compressed gas or actively by a supply or pneumatically. The commercially available types of nozzle provide a large variety of geometrical spray patterns. According to the present invention, those types of nozzle are preferred which produce an almost rectangular spray pattern because the microscope slide can be passed under such a nozzle on an infinitely variable conveyor belt and only a relatively small part of the spray pattern must be covered over by a mask.

Thus, the present invention also provides a device for the large-scale production of pre-coated microscope slides, comprising an infinitely variable conveyor belt, a regulatable spraying apparatus and a mask.

Since the dyestuff used according to the present invention are usually sprayed on in the form of solutions of low viscosity in very fine and very uniform distribution, the two-component spraying process is preferred. This process has the further advantage that the gas stream rapidly removes the solvent vapors and thus the drying process commences immediately after impingement of the dyestuff solution on to the microscope slide. We have found that microscope slides produced according to this process do not require any subsequent drying and can be removed for packing directly from the end of the conveyor belt.

It is, of course, in principle also possible, instead of moving the microscope slides, to move the spraying apparatus at a constant speed over previously prepared microscope slides lying next to one another but it is less expensive to install a stationary spray apparatus and to pass the microscope slides on a conveyor belt under the nozzle.

The amount of dyestuff sprayed on depends upon the spraying angle, the distance of the nozzle from the microscope slides, the concentration of the spray solution, the amount of liquid passing through the nozzle and the speed of the conveyor belt. Furthermore, the droplet size is also influenced by the type of nozzle, as well as the gas pressure and the viscosity of the spray solution.

The optimum conditions for any particular formulation can thus, in part, be calculated in advance and, in part, can be determined experimentally in a simple manner and are to be adapted to the particular formulation.

The dyestuffs used can be practically all the dyestuffs and dyestuff mixtures conventionally employed for biological staining. Typical examples are the Nile blue sulfate staining of Heinz intracorpuscular bodies, the Sternheimer-Malbin staining (gentian violet and safranin) of urine sediment, the Seyderhelm staining (trypan blue and Congo red) for leukocyte differentiation in urine sediment, the blood count according to Seeman's method with neutral red and Janus green B, the staining of starch in gastric juice with Lugol's reagent (potassium iodide-iodine), as well as the fuchsine staining of bacteria in urine. Of quite special interest are microscope slides pre-coated with new methylene blue (methylene blue N) and cresyl violet acetate for staining erythrocytes and leukocytes for differential blood counts.

Insofar as the stainings are thereby not influenced, the spray solution can, of course, also contain additives, such as anti-coagulants, buffers, solubilizing agents, preserving agents, surface-active materials and the like.

As solvents, there can be used, in particular, water, lower alcohols, ketones, esters and halogenated hyrocarbons, as well as mixtures thereof. The only important thing is that the dyestuffs or dyestuff mixtures or the other components are sufficiently soluble therein and that the solvents evaporate sufficiently quickly. If the dyestuffs are not sufficiently soluble, then ultra-fine dispersions can also be employed, such as are obtained, for example, by the use of ultra-sonic waves.

Furthermore, the process and device according to the present invention permit different dyestuffs to be applied in separate spraying operations when, for example, they cannot be jointly brought sufficiently into solution in any solvent or when, for example, they tend to undergo chemical reaction or to precipitate. In such cases, over the conveyor belt carrying the microscope slides, there are arranged two successive spray devices from which the various dyestuffs or other adjuvants can then be successively applied.

The finished sprayed microscope slides can, if desired, be subsequently further dried by passing the conveyor belt through a drying tunnel. When using, according to the present invention, two-component nozzles, this process step is, however, generally unnecessary so that the microscope slides can be removed directly from the end of the conveyor belt and packed, the cassette for microscope slides described in U.S. application Ser. No. 659,819, filed Feb. 20, 1976 having proved to be especially useful for packing.

With the use of the process and device according to the present invention, it is now, for the first time, possible to produce, on a large scale, pre-colored microscope slides of uniform quality, continuously and in large numbers so that manual staining can now be replaced by the use of pre-coated microscope slides. A further advantage of the process according to the present invention is that not only glass microscope slides but also microscope slides made from transparent synthetic resins which are difficult to wet can also be used.

For satisfactory storage and packing, it is recommended after the spraying, to apply labels to the ends of the rectangular microscope slides, which labels not only permit a satisfactory identification but also prevent sticking of the plates or scratching of the dyestuff layer. Therefore, the device according to the present invention is preferably coupled with a labelling device, as well as with a packing machine. Furthermore, it is also advisable to couple the spraying unit with a conventional destacking device for microscope slides, as well as with a unit for continuously washing and drying the microscope slides prior to coating. The washing unit also simultaneously ensures a continuous cleaning of the conveyor belt.

In the simplest case, the spray mask can consist of two metal strips which are arranged as closely as possible to the microscope slides. In order to have to clean the masks as infrequently as possible, they can be provided with a small drainage trough. Other solutions to the problem consist of a pair of continuously but more slowly running paper strips or metal bands.

The following Examples are given for the purpose of illustrating the present invention:

EXAMPLE 1

Device for the large-scale production of pre-coated microscope slides — FIGS. 1-3:

From a known type of destacking device 7, microscope slides were taken off transversely from stack 1 in the direction of movement of a conveyor belt 8 in such a manner that they practically touch one another without an intermediate space. The speed of the conveyor belt 8 was infinitely variable. Below a spray nozzle 10 and above the microscope slides, there was provided a mask 12 (FIG. 2) which determined the breadth of the part of the microscope slides 13 to be sprayed. Above the mask, there was arranged a two-component broad spray nozzle 10, the spraying angle and distance of which ensured a breadth of spraying which was somewhat greater than the breadth of the mask. Before entry into the spraying zone, the microscope slides on the conveyor belt 8 passed through washing and rinsing zones 2 and 3 and air drying zone 4. The microscope slides 13 emerging from the spraying zone were labelled on both ends of a labelling machine 6 and passed from there into a conventional packing machine.

FIG. 3 of the drawing shows a preferred spray nozzle 10 wherein the dyestuff can be sprayed as fed via bore 26 where it exits from the centrally positioned portion of the spray head 20. Air for atomizing the dyestuff is fed via bore 30 and compressed air for providing the desired spray pattern or geometry is fed via bore 28 and 22 and exit from openings 24.

EXAMPLE 2

A solution of the following composition was prepared, using chromatographically pure dyestuffs (cf, U.S. application Ser. No. 672,572 filed Mar. 31, 1976):

methylene blue N hydrochloride — 130 mg.
cresyl violet acetate — 270 mg.
methanol — as 100 ml.

This solution was sprayed from a 0.5 mm. wide spray nozzle (SS 60 67228-45 of the firm Spraying Systems) with a spray angle of about 25° and at a distance of 20 cm. through a mask in a breadth of 3 cm. on to microscope slides which were passed below the nozzle at a speed of 1.5 m./minute. Subsequent drying of the sprayed microscope slides was not necessary. The spray pressure was 1.2 ats. and the fluid throughput through the nozzle was 10 ml./minute.

In the case of an average droplet size about 20 μ, the amount of dyestuff applied was about 3 μg./cm$^2$.

A drop of blood with a volume of about 5 - 10 μl. was applied to a pre-colored microscope slide produced in this manner and covered with a cover slip. After about 3 to 5 minutes, the staining was assessed under a microscope at about 800 fold magnification, using an oil immersion objective. The individual particles of the blood have the following stainings:

reticulocytes : purple-colored reticulum within the scarcely colored erythrocytes
neutrophils : purple-colored nucleus within a fine granulated, almost colorless plasma
eosinophils : purple-colored nucleus within a coarsely granulated yellow plasma
basophils : dark purple-colored nucleus within an average-sized, compact granulated orange-red-colored plasma
lymphocytes : purple-colored nucleus with bright purple-colored plasma
monocytes : as lymphocytes but larger and more plasma
thrombocytes : small purple-colored particles.

EXAMPLE 3

A 1% ethanolic solution of brilliant cresyl blue was sprayed on to microscope slides in the manner described in Example 2, a dyestuff application of about 6 μg./cm$^2$ being obtained.

A drop of blood with a volume of about 5 - 10 μl. was applied to a so-produced pre-colored microscope slide and covered with a cover slip.

After about 5 minutes, the staining is assessed under a microscope at about 800 fold magnification. The reticulocytes hereby appear as erythrocytes with a dark blue reticulum.

If, instead of brilliant cresyl blue, there was used the same amount of Nile blue sulfate, then, in addition to the reticulocytes, the Heinz intracorpuscular bodies of the erythrocytes were also stained blue.

EXAMPLE 4

A solution of the following composition was produced, while irradiating with ultrasonic waves:
toluidine blue O — 1000 mg.
polyoxyethylene sorbitan monopalmitate (Tween 80) — 30 mg.
distilled water — ad 100 ml.

This solution was sprayed on to microscope slides in the manner described in Example 2, the amount of dyestuff thus applied being about 6 μg./cm$^2$.

A drop of blood with a volume of about 5 - 10 μl. was applied to a so-produced microscope slide and covered with a cover slip. After about 10 minutes, the staining was assessed under a microscope at about 800 fold mangification, using an oil immersion objective. The staining characteristics of the blood particles were identical with those described in U.S. Pat. No. 3,906,120.

EXAMPLE 5

A commercially available solution of crystal violet and alcian blue (Sedicolor) was sprayed on to microscope slides in the manner described in Example 2.

A small droplet of a stirred up urine sediment was applied to the microscope slide and examined microscopically at a magnification of 400.

The individual urine components were identified by their characteristics form and by the following stainings:
erythrocytes : pale pink to violet
leukocytes : epithelial plaque: pink with violet to blue nuclei
kidney epithelia : violet with violet to blue nuclei
mucus : bright blue to petroleum blue
hyaline cylinders : bright blue to petroleum blue
wachs cylinders : violet to purple-red
cellular cylinders : bright blue to petroleum blue ground substance with the characteristics staining of the cellular inclusions (e.g. leukocytes and the like).

What is claimed is:

1. Process for the large-scale production of pre-coated microscope slides which comprises spraying dyestuff solution on to microscope slides in the form of individual microfine dyestuff droplets thereon which do not flow together.

2. Process of claim 1 wherein the microscope slides are passed at a constant speed under a spray nozzle, the spray pattern of which is kept rectangular by means of a mask.

3. Process of claim 1 wherein the dyestuff solution is sprayed from a two-component nozzle.

4. Process of claim 1 wherein the dyestuff solution also contains at least one member selected from the group of anticoagulants, buffers, solubilizing agents, preserving agents and surface-active materials.

5. Process of claim 1 wherein the dyestuff solution contains, as solvent, water, a lower alcohol, a ketone, an ester or a halogenated hydrocarbon or a mixture thereof.

6. Process according to claim 3, wherein one component of the two-component nozzle is a gas stream and wherein the dyestuff solution is immediately dried upon impingement by the gas stream to completely dry the dyestuff solution without a further drying step.

* * * * *